United States Patent [19]

Bowen et al.

[11] Patent Number: 4,529,868
[45] Date of Patent: Jul. 16, 1985

[54] SOFT CONTACT LENS DISINFECTING UNIT

[75] Inventors: John G. Bowen, 11521 Heathcliff Dr., Santa Ana, Calif. 92705; Stephen G. Hauser, Tarzana, Calif.

[73] Assignee: John G. Bowen, Marina del Rey, Calif.

[21] Appl. No.: 448,281

[22] Filed: Dec. 9, 1982

Related U.S. Application Data

[63] Continuation-in-part of Ser. No. 317,071, Nov. 2, 1981, abandoned.

[51] Int. Cl.³ .......................... H05B 3/06; A61L 2/04
[52] U.S. Cl. .................................... 219/521; 219/386; 219/439; 219/505; 219/541; 422/38; 422/119; 422/307
[58] Field of Search ............... 219/214, 385, 386, 328, 219/401, 430, 433, 437, 438, 439, 441, 504, 521, 505, 541; 422/22, 38, 119, 155, 199, 307, 300; 338/22 R, 225 D

[56] References Cited

U.S. PATENT DOCUMENTS

| | | | |
|---|---|---|---|
| 3,666,914 | 5/1972 | Dean | 219/214 |
| 3,983,362 | 9/1976 | Hoogesteger et al. | 219/521 |
| 4,044,226 | 8/1977 | Kadlecik et al. | 219/521 |
| 4,158,126 | 6/1979 | Seitz | 219/439 |
| 4,178,499 | 12/1979 | Bowen | 219/439 |
| 4,270,039 | 5/1981 | Hauser | 219/439 |
| 4,302,664 | 11/1981 | Ryder et al. | 219/504 |
| 4,341,948 | 7/1982 | Sundström et al. | 219/521 |
| 4,369,355 | 1/1983 | Helixon | 219/521 |
| 4,379,965 | 4/1983 | Dounce et al. | 219/521 |
| 4,388,521 | 6/1983 | Thomas et al. | 219/521 |

Primary Examiner—Volodymyr Y. Mayewsky
Attorney, Agent, or Firm—Keith D. Beecher

[57] ABSTRACT

An electrically energized evaporator and/or soft lens heating and disinfecting unit is provided which is compact in size in that it does not require a separate holder for the lenses. Instead, the unit itself forms the lens holder, and the holder has compartments for the left and right lenses and which are adapted to be filled with an appropriate saline solution, the compartments being heated by electrical heating elements to perform the desired disinfecting and sterilizing functions. These heating elements may take the form of positive temperature coefficient (PTC) elements. The unit is equipped with an electric plug which may be directly plugged into an electric receptacle to energize the heating elements.

9 Claims, 9 Drawing Figures

U.S. Patent  Jul. 16, 1985  Sheet 1 of 3  4,529,868
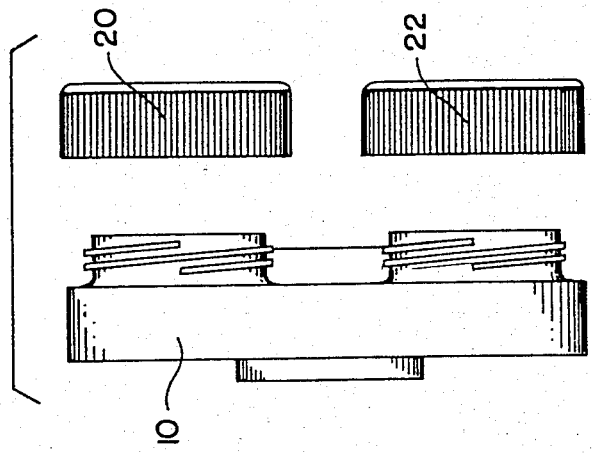
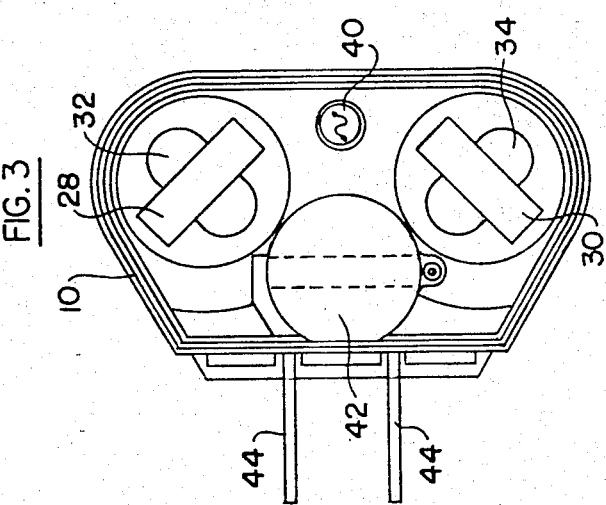
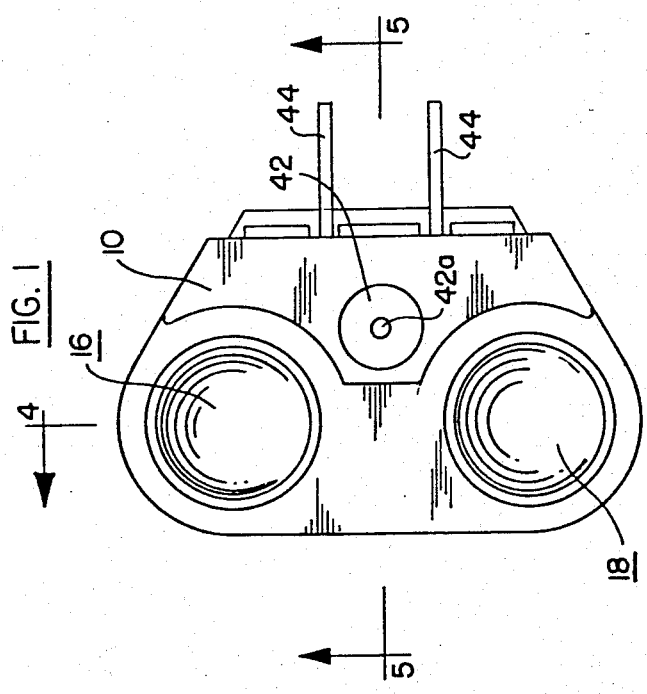

SOFT CONTACT LENS DISINFECTING UNIT

This application is a continuation-in-part of copending application Ser. No. 317,071, filed Nov. 2, 1981, abandoned, in the name of the present inventors.

BACKGROUND OF THE INVENTION

Previously, hard contact lenses were the only type available, and while such lenses required cleaning, sterilization was not a particular problem. The soft contact lenses which have now been developed are made from a porous plastic material which absorbs water, and upon doing so becomes soft and pliable. While hard lenses must be cleaned and sterilized periodically, the need for sterilization of the soft lenses is more acute, this being due to the porous nature of the plastic material which provides a medium for bacteria. Therefore, the soft contact lenses should be cleaned and sterilized on a regular basis, perhaps daily.

Since the soft lens material is permeable to liquids, soaking soft lenses in strong germicidal solutions for sterilizing purposes is not desirable. This is because such soaking will result in the lense becoming impregnated with the solution, and this can lead to irritation to the eyes when the lenses are worn. In general, it has been found difficult, if not impossible, to disinfect soft lenses by treatment with chemical or biochemical solutions since such solutions have been found to cause eye irritation to at least a substantial percentage of the users.

Accordingly, another sterilization method has been developed for soft lenses, and which involves placing the lenses in a saline solution, and the heating of the saline solution to a temperature sufficiently high to destroy any bacteria that might be present on the lenses. In carrying out this method, and in accordance with the prior art practice, the lenses are placed in a case which contains the saline solution, and the case is placed in a second vessel containing water, or other fluid, which is heated by any appropriate heating element. Or, alternately, the lenses are disposed within the case containing the saline solution, and the case is placed in direct contact with the heating element.

The unit of the present invention goes a step further, and provides for the case itself, which contains the saline solution, to be incorporated into the housing for the heating element, so that a compact unit may be provided which can be easily carried about by the user.

As mentioned above, for disinfecting soft contact lenses, the heat of the saline solution must be raised to an elevated temperature sufficient to destroy any bacteria that might be in the lens, and the heating unit must hold the temperature of the lens at or above that temperature for the required time, and then allow the temperature to cool to ambient level. Typical values of the time and temperature deemed suitable for disinfecting soft contact lens require the lens to be maintained at or above 80° C. for a period of 10 minutes or more. Since aging of the lens material is accelerated by excessive temperatures and/or by extended time at elevated temperatures, it is desirable that the heating unit be controlled so that excessive temperatures, or excessive time at elevated temperatures will not shorten the life of the lens. This is achieved by the unit described in U.S. Pat. No. 4,158,126, which is licensed to the present assignee.

The sterilization unit of the present invention is of the same general type described and claimed in U.S. Pat. No. 4,158,126, and like the unit described in the patent, uses a fluid, such as wax to transmit heat from the heating element to the saline solution containing case for the contact lenses. However, as described above, the unit of the present invention, unlike the unit described in the patent, and unlike other prior art contact lense disinfecting units, provides for the contact lens case to be part of the heating unit, so that a compact unit may be provided which is readily portable, and which may be carried, for example, in a purse or handbag.

BRIEF DESCRIPTION OF THE DRAWINGS

FIG. 1 is a top plan view of the upper housing of a unit constructed in accordance with one embodiment of the invention, and with the covers of the unit removed;

FIG. 2 is a side-view of the upper housing of the unit, showing the covers displaced from the top of the upper housing;

FIG. 3 is a bottom view of the upper housing of the unit revealing the components mounted within the upper housing;

DETAILED DESCRIPTION OF THE ILLUSTRATED EMBODIMENT

Figure 4:
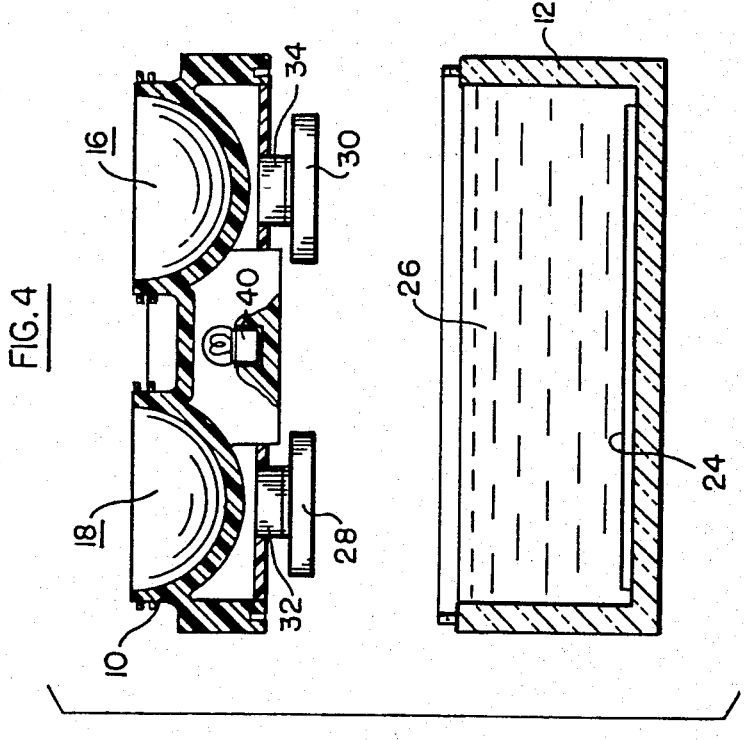
FIG. 4 is a section of the upper housing taken along the line 4—4 of FIG. 1, and also showing the lower housing displaced from the upper housing.

The heating unit illustrated in the drawings includes an upper housing 10 formed of any appropriate plastic material, and a lower housing 12 (FIG. 4) which is preferably formed of a transparent plastic material.

The upper housing is configured to define a pair of adjacent wells 16 and 18 each of which is intended to be filled with an appropriate saline solution, so that the left lens may be placed in one of the wells, and the right lens may be placed in the other. When the lenses are placed in the saline solutions in the wells, covers 20 and 22 (FIG. 2) are screwed down over the tops of the wells.

The upper housing 10 is fitted down over the lower housing 12, and the two housings are bonded together. A red indicator sheet 24 is affixed to the bottom of the lower housing (FIG. 4), and the lower housing is filled with an appropriate fluid such as paraffin wax 26.

A pair of heating elements 28 and 30 are mounted in the upper housing 10 under the corresponding wells 16 and 18, and thermal cut-off switches 32 and 34 are mounted on the respective heating elements. The thermal cut-off switches serve to de-energize the unit whenever the temperature at the particular cut-off switch reaches a predetermined threshold level.

A light bulb 40 is also mounted in the upper housing, and it is illuminated when the unit is energized. When the wax 26 is melted, it becomes transparent, so that the bulb 40 causes a red glow to emanate from the bottom of the lower housing 12, due to the red indicator sheet 24, to indicate intervals when the unit is actually energized. Also, the red indicator sheet 24 is visible through the side walls of the transparent lower housing 12 when the wax 26 is molten, to indicate that the wax is in a molten state.

The unit also includes a switch 42 which has a pushbutton 42a protruding through the top of the upper housing, as shown in FIG. 1, and the switch is closed when the pushbutton 42a is depressed. The unit has a pair of electrically conductive blades 44 protruding from one side constituting an electric plug, which enable the unit to be plugged directly into an electrical receptacle.

Figure 5:
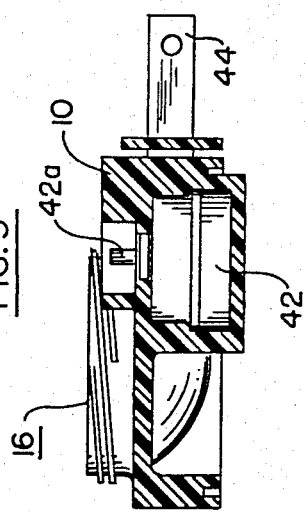
FIG. 5 is a section of the upper housing taken along the line 5—5 of FIG. 1.
Figure 6:
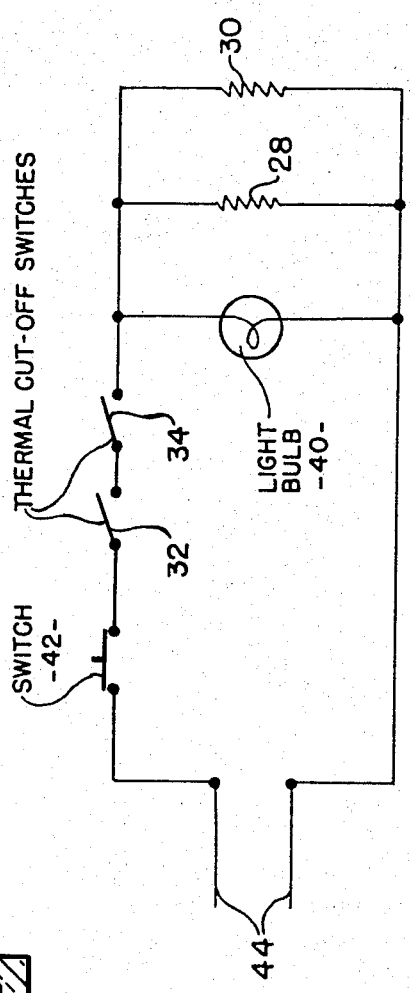
FIG. 6 is a circuit diagram showing the connections to the various electrical elements within the unit.

The various electrical elements in the unit are connected in the manner shown in FIG. 6.

In order to sterilize a pair of soft lenses, the electric plug formed by blades 44 is plugged into an electrical receptacle, and an appropriate saline solution is placed in the wells 16 and 18. The left eye and right eye lenses are then inserted in the wells, and the covers 20 and 22 are screwed in place. The pushbutton 42a is then depressed to close switch 42, and light bulb 40 is illuminated to indicate that the unit is in an energized state.

The heating elements 28 and 30 are of the resistance type, and they continue to heat up so long as switch 42 is closed. As the heating elements 28 and 30 are energized, the wax within the housing becomes molten, and the red indicator 24 can be viewed through the side wall. A predetermined time after the indicator becomes visible, the switch 42 is opened by again pressing pushbutton 42a, and the unit gradually cools down, with the temperature of the saline solution being sufficient to sterilize the lenses.

Should the temperature of either heating element 28 or 30 rise above a predetermined threshold, the corresponding thermal cut-off switch 32 or 34 is operated to de-activate the unit.

Figure 7:
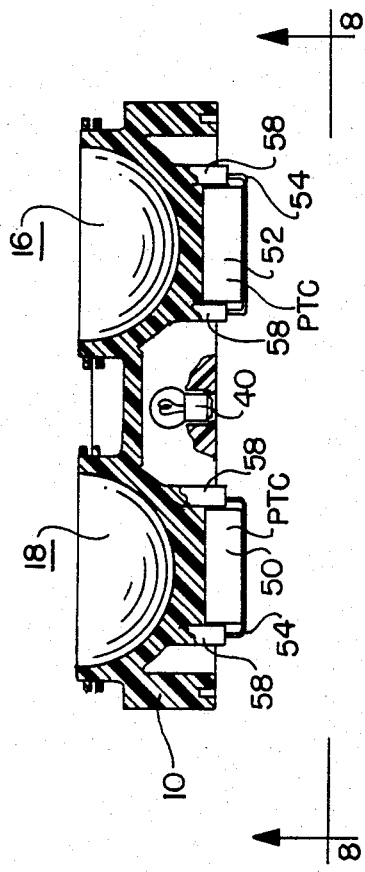
FIG. 7 is a section, like FIG. 5, but using PTC's as the heating elements.
Figure 8:
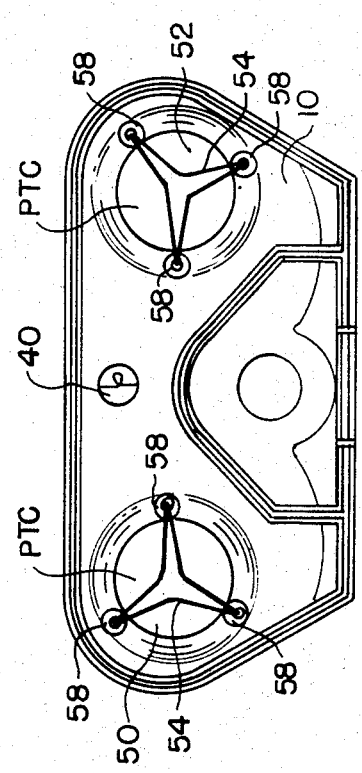
FIG. 8 is a bottom view taken along the line 8—8 of FIG. 7.

In the embodiment of FIGS. 7 and 8, the heating elements of the previous embodiment are replaced by PTC elements 50 and 52. As is well known, PTC elements will heat to a predetermined temperature when an electric current is passed through them, and when that temperature is reached their resistance increases abruptly, so that they act as their own temperature regulators.

In the second embodiment, the PTC elements 50, 52 are mounted directly against the wall of wells 16 and 18 by wires 54, 56 which are mounted in posts 58.

Figure 9:
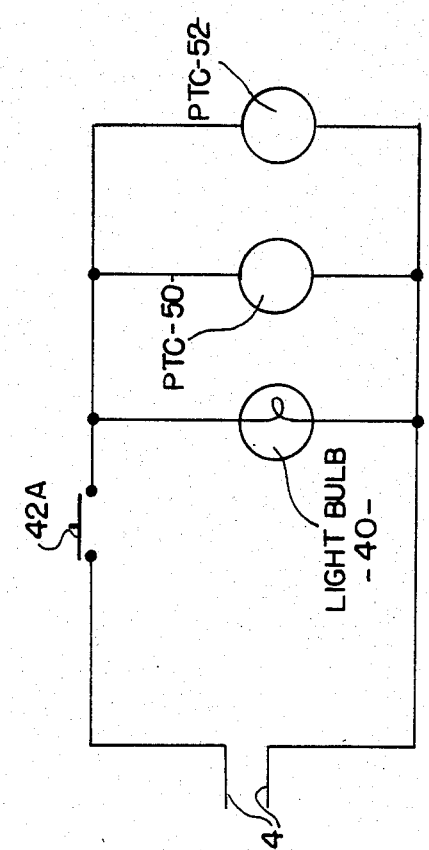
FIG. 9 is a circuit diagram of the embodiment of FIGS. 7 and 8.

As shown in FIG. 9, the PTC elements 50 and 52 are mounted in parallel with bulb 40, and the cut off switches 32 and 34 of FIG. 6 are not required.

The unit of FIGS. 7 and 8 may also be used as a medicinal evaporator, in which case an appropriate liquid is placed in the wells and an on-off switch 42A is closed. The on-off switch is not really necessary except as a convenience for the vaporizer since it enables the unit to be plugged into the electric receptacle, filled with the liquid to be evaporated while still cold, and then the switch 42A may be turned on. The PTC elements can be used with or without the paraffin.

The invention provides, therefore, a simple portable compact heating unit for soft contact lenses which receives the lenses directly, and which is small enough to fit in a purse or handbag.

It will be appreciated that while a particular embodiment of the invention has been shown and described, modifications may be made. It is intended in the claims to cover all modifications which come within the true spirit and scope of the invention.

What is claimed is:

1. An electrically energized heating unit for evaporating a medicinal liquid, for disinfecting soft lenses, and the like, comprising: a housing of plastic material having an upper section and a lower section, and having two wells formed in the external surface of the upper section adjacent to one another for receiving a saline solution and for receiving a pair of lenses to be disinfected; a pair of removable covers mounted on the respective wells; a pair of electrically conductive blades mounted on one wall of the lower section of the housing and protruding outwardly therefrom to form an electric plug to be received in an electrical receptacle; electrically energized heater means mounted in the lower section of the housing adjacent to the internal surfaces of the wells; and electric circuitry mounted within the lower section of the housing for connecting the heater means to the electrically conductive blades.

2. The electrically energized heating unit defined in claim 1, in which the lower section of the housing is filled with wax which becomes molten after a particular time interval following the energization of the heater means.

3. The electrically energized heating unit defined in claim 1, in which said heater means comprises first and second heater elements mounted in the lower section of said housing adjacent to the inner surfaces of respective ones of the wells.

4. The electrically energized heating unit defined in claim 3, and which includes first and second thermal cut-off switches connected to and mounted adjacent to respective ones of the heater elements to de-energize the unit should the temperature of either of the heater elements exceed a particular threshold.

5. The electrically energized heating unit defined in claim 2, in which said housing comprises an upper opaque section and a lower transparent section.

6. The electrically energized heating unit defined in claim 5, and which includes a colored indicator sheet mounted in said lower section to become visible through the wall of said lower section when the wax in the housing is in a molten state.

7. The electrically energized heating unit defined in claim 6, and which includes an electric lamp mounted in said upper housing and connected to said circuitry to be energized when the unit is energized and to illuminate said colored sheet when the wax in the housing is in its molten state.

8. The electrically energized heating unit defined in claim 1, in which said electrically energized heater means comprises at least one positive temperature coefficient element.

9. The electrically energized heating unit defined in claim 1, in which the heater means comprises a pair of positive temperature coefficients heater elements mounted in said housing in contact with the interior walls of said wells.

* * * * *

REEXAMINATION CERTIFICATE (1903rd)
United States Patent [19]

Bowen et al.

[11] B1 4,529,868

[45] Certificate Issued  Jan. 19, 1993

[54] SOFT CONTACT LENS DISINFECTING UNIT

[75] Inventors: John G. Bowen, Santa Ana; Stephen G. Hauser, Tarzana, both of Calif.

[73] Assignee: The Cooper Companies, Inc., Palo Alto, Calif.

Reexamination Request:
No. 90/002,012, Apr. 27, 1990

Reexamination Certificate for:
Patent No.: 4,529,868
Issued: Jul. 16, 1985
Appl. No.: 448,281
Filed: Dec. 9, 1982

Related U.S. Application Data

[63] Continuation-in-part of Ser. No. 317,071, Nov. 2, 1981, abandoned.

[51] Int. Cl.[5] .................... H05B 3/06; A61L 2/04
[52] U.S. Cl. .................... 219/521; 219/386; 219/439; 219/505; 219/541; 422/38; 422/119; 422/307
[58] Field of Search .............. 219/385, 386, 521, 504, 219/505

[56] References Cited

U.S. PATENT DOCUMENTS

| | | | |
|---|---|---|---|
| 3,666,914 | 5/1972 | Dean | 219/214 |
| 3,983,362 | 9/1976 | Hoogesteger | 219/521 |
| 3,998,590 | 12/1976 | Glorieux | 422/117 |
| 4,044,226 | 8/1977 | Kadlecik | 219/521 |
| 4,158,126 | 6/1979 | Seitz | 219/439 |
| 4,178,499 | 12/1979 | Bowen | 219/439 |
| 4,270,039 | 5/1981 | Hauser | 219/439 |
| 4,302,664 | 11/1981 | Ryder | 219/504 |
| 4,341,948 | 7/1982 | Sundstrom | 219/521 |
| 4,369,355 | 1/1983 | Helixon | 219/521 |
| 4,379,965 | 4/1983 | Dounce | 219/521 |
| 4,388,521 | 6/1983 | Thomas | 219/521 |

FOREIGN PATENT DOCUMENTS 2369847 6/1978 France .
2416492 8/1979 France .

*Primary Examiner*—Teresa J. Walberg

[57]  ABSTRACT

An electrically energized evaporator and/or soft lens heating and disinfecting unit is provided which is compact in size in that it does not require a separate holder for the lenses. Instead, the unit itself forms the lens holder, and the holder has compartments for the left and right lenses and which are adapted to be filled with an appropriate saline solution, the compartments being heated by electrical heating elements to perform the desired disinfecting and sterilizing functions. These heating elements may take the form of positive temperature coefficient (PTC) elements. The unit is equipped with an electric plug which may be directly plugged into an electric receptacle to energize the heating elements.

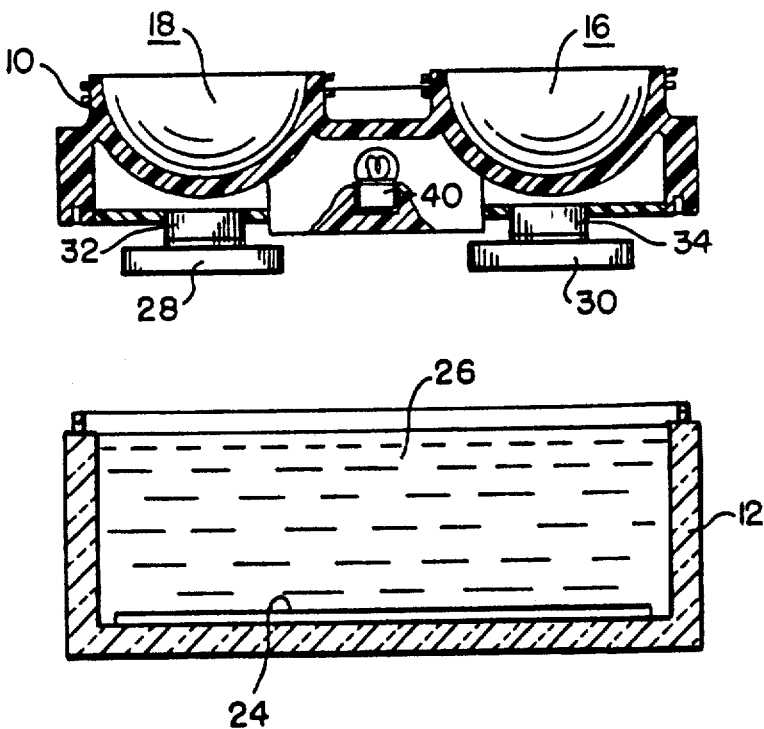

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claim 4 is confirmed.

Claims 1-3 and 5-9 are cancelled.

4. The electrically energized heating unit defined in claim 3, and which includes first and second thermal cut-off switches connected to and mounted adjacent to respective ones of the heater elements to de-energize the unit should the temperature of either of the heater elements exceed a particular threshold.

* * * * *